United States Patent [19]

Bordoni et al.

[11] Patent Number: 4,598,704
[45] Date of Patent: * Jul. 8, 1986

[54] AEROSOL INHALATION DEVICE

[75] Inventors: Maurice E. Bordoni, Westtown; Ephraim Lieberman, Suffern, both of N.Y.

[73] Assignee: Cadema Medical Products, Inc., Middletown, N.Y.

[*] Notice: The portion of the term of this patent subsequent to Apr. 16, 2002 has been disclaimed.

[21] Appl. No.: 707,387

[22] Filed: Mar. 1, 1985

Related U.S. Application Data

[60] Division of Ser. No. 642,718, Aug. 22, 1984, Pat. No. 4,510,929, which is a continuation of Ser. No. 360,370, Apr. 30, 1982, abandoned.

[51] Int. Cl.$^4$ ............................................. A61M 11/00
[52] U.S. Cl. ............................ 128/200.14; 128/200.18
[58] Field of Search ............... 128/200.14, 200.18, 128/200.19, 200.21, 654, 203.12, 203.15

[56] References Cited

U.S. PATENT DOCUMENTS

| | | | |
|---|---|---|---|
| 3,762,409 | 10/1973 | Lester | 128/200.14 |
| 3,990,442 | 11/1976 | Patneau | 128/200.14 |
| 4,206,160 | 6/1980 | Suddendorf et al. | 128/200.14 X |
| 4,232,667 | 11/1980 | Chalon et al. | 128/203.12 X |
| 4,259,951 | 4/1981 | Chernack et al. | 128/200.14 |
| 4,333,450 | 6/1982 | Lester | 128/200.14 |
| 4,391,271 | 7/1983 | Blanco | 128/203.12 |
| 4,396,015 | 8/1983 | Johnson | 128/200.14 |
| 4,510,929 | 4/1985 | Bordoni et al. | 128/200.14 |

Primary Examiner—Edward M. Coven
Attorney, Agent, or Firm—Leonard Bloom

[57] ABSTRACT

A disposable aerosol inhalation device for use in producing properly sized radioactive tagged particles. A mouthpiece is attached to a wye connector containing a valving system for inhalation of the radioactive aerosol and exhalation to an entrapping filter. Conduits are respectively provided by flexible tubing to a nebulizer and to the filter. The optimum range of particle sizes is generated by producing an aerosol from the nebulizer having an internal baffle. For ease of handling and to minimize radiation exposures, an entry is provided to add radioactive solution directly into the baffled nebulizer. To further reduce radiation exposure, the baffled nebulizer and entrapping filter are housed in a leaded enclosure. A method, which may be carried out using the device and the leaded enclosure involves introducing radioactive solution into the nebulizer to generate an aerosolized mist containing radioactive tagged particles of less than substantially two microns.

18 Claims, 4 Drawing Figures

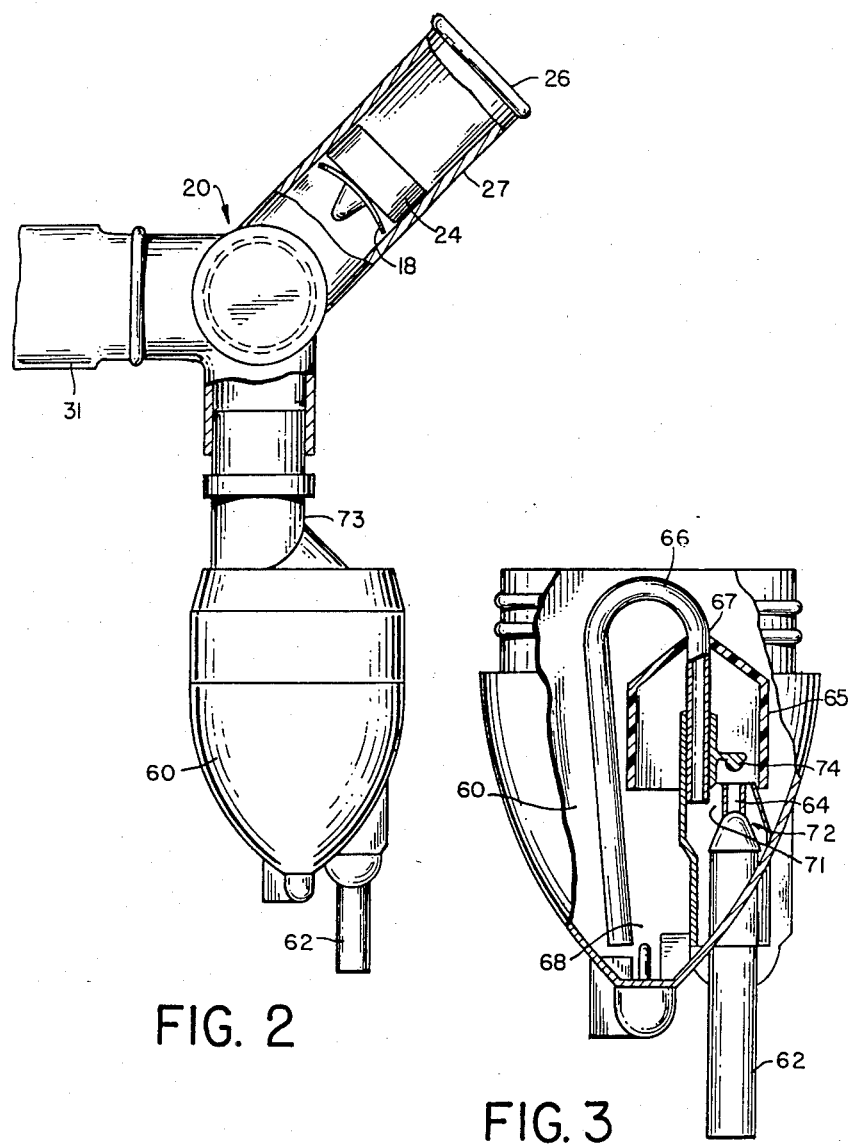

४,598,704

AEROSOL INHALATION DEVICE

CROSS REFERENCE TO RELATED APPLICATIONS

This application is a division of application Ser. No. 642,718 filed on Aug. 22, 1984, now U.S. Pat. No. 4,510,929, and entitled, "Disposable Radioactive Aerosol Inhalation Apparatus" which is a file wrapper continuation of application Ser. No. 360,370 filed on Apr. 30, 1982 and entitled, "Disposable Aerosol Inhalation Apparatus", abandoned.

BACKGROUND OF THE INVENTION

This invention relates to a radioactive aerosol inhalation apparatus which includes a disposable pulmonary inhalation device which is comprised of a means to generate properly sized radioactive particles for subsequent inhalation. For various types of diagnostic testing and treating, it is necessary to have patients inhale radioactive materials in order, for example, to perform ventilation studies of the lung. In addition, it is well known that the hospital staff who handle radioactive materials need protection against the problems associated with ionizing radiation exposure and this apparatus provides for adequate shielding to meet this requirement. For flexibility, the apparatus is portable, the device is disposable, and the apparatus is inexpensive. The apparatus provides the capability to easily and safely add the radioactive solution to the nebulizer, for aerosolizing the radioactive solution to the proper particle size, and to collect the radioactive particles in a properly shielded filter.

This technique of administering a radioactive aerosol is an improvement over existing modalities in that the radiation dose to the patient is less, the probability of radioactive contamination within the hospital room, as compared to other techniques is diminished, and the flexibility to obtain images of various anatomical positions of the patient is increased.

Relevant prior art United States Letters Patents are:

| U.S. Pat. No. | Inventor(s) | Date Issued |
|---|---|---|
| 3,695,254 | Blum | Oct. 3, 1973 |
| 3,762,409 | Lester | Oct. 2, 1973 |
| 3,769,967 | Jones et al. | Nov. 6, 1973 |
| 3,881,463 | Le Mon | May 6, 1975. |

SUMMARY OF THE INVENTION

The invention as disclosed in the above-mentioned parent applications relates to a new and improved aerosol inhalation method and apparatus which generates properly sized radioactive particles for performing ventilation studies of the lungs. A radioactive solution is added to a baffled nebulizer and the solution aerosolized using air or oxygen. The aerosolized radioactive particles are then breathed into the lungs and data for assessing lung function may be recorded by means of a radiation particle counting device such as a scintillation camera and associated software. The radioactive aerosol is administered to the patient through a mouth-piece or face mask via a conduit of valved flexible tubing, the valving being in close proximity to the mouthpiece to minimize the volume of the passages from the valve head to the mouthpiece.

It is, therefore, a principal object of the invention as disclosed in the parent applications to provide an apparatus which includes a disposable radioactive aerosol inhalation device capable of allowing pulmonary ventilation test that deliver proper-sized particles to lung areas, controlled delivery and recovery of radioactive aerosolized particles and shielding to minimize exposure of personnel to problems associated with ionizing radiation.

Another object of the invention disclosed in the parent applications is to provide an apparatus that incorporates a valve which is activated during the breathing cycle of the patient to assist in permitting the patient to inhale with the minimum of effort during the generation of radioactive aerosol from within the system.

Another object of the invention disclosed in the parent applications is to provide a shielded portal to permit the safe and rapid addition of radioactive solution into the baffled nebulizer. The injection site is through a valve diaphragm that is positioned at an approximate 45 degree angle from the top of the baffled nebulizer.

A still further object of the invention disclosed in the parent applications is to provide an apparatus of the character described which will minimize the radiation exposure to the patient and technician administering the diagnostic test. Adequate shielding in the form of lead surrounds the baffled nebulizer and entrapping filter, reducing the problems associated with exposures to ionizing radiation.

Another object of the invention disclosed in the parent applications is to provide an apparatus of the character described in which images or pictures from various anatomical positions can be taken further increasing the usefulness of this diagnostic method of evaluating disease of the bronchus, the bronchioles, and the alveolar sites of the lung.

A further object of the invention disclosed in the parent applications is to provide an apparatus of the character described which will reduce the radioactive contamination of the facilities, the equipment, and most importantly, the attending medical personnel.

An object of the present invention is to provide an aerosol inhalation device which generates an aerosol mist and entrappes exhaled aerosol.

Other features and advantages of the invention will become more readily apparent from the following detailed description, when taken in conjunction with the accompanying drawings.

BRIEF DESCRIPTION OF THE DRAWINGS

FIG. 2 is a fragmentary perspective diagramatic view of a portion of the apparatus of FIG. 1 illustrating the angulated wye and valve through which radioactive solution is added to the baffled nebulizer.

FIG. 3 is a fragmentary perspective diagramatic view of a portion of the apparatus of FIG. 1 illustrating the modified nebulizer with its internal baffle.

DESCRIPTION OF THE PREFERRED EMBODIMENT

Figure 1:
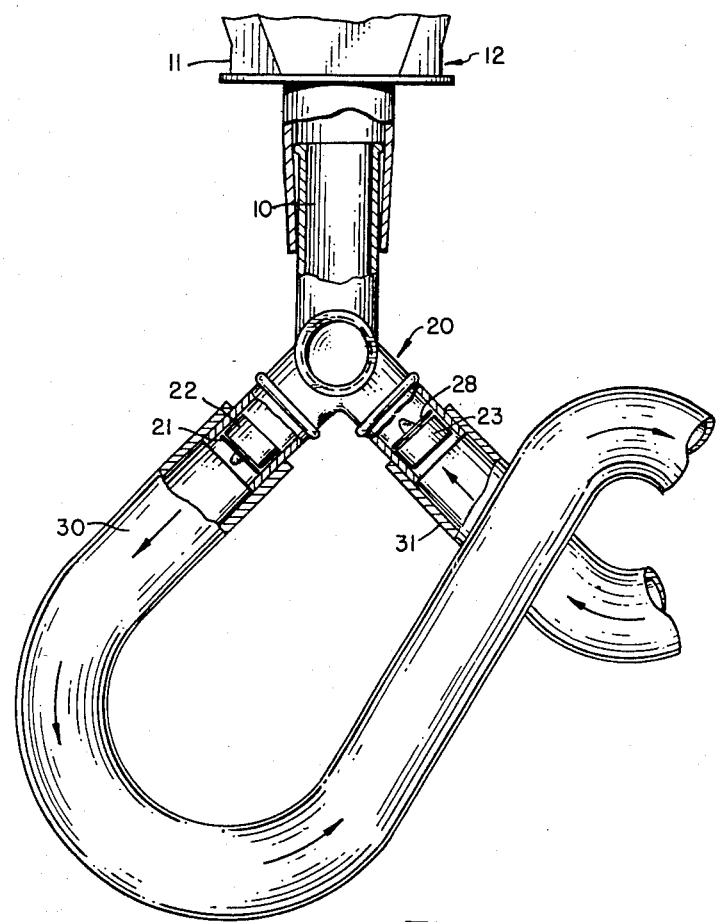
FIG. 1 is an elevational diagramatic perspective view of the aerosol inhalation apparatus constructed in accordance with the invention disclosed in the parent applications.

Referring to FIG. 1, there is shown a disposable aerosol inhalation device for use in producing radioactive tagged particles in accordance with an embodiment of the invention disclosed in the parent applications. A patient (not shown) breathes through a mouthpiece 12 having flanges 11 to permit a tight fit in the mouth. The mouthpiece is attached to a tubular extension 10 of a wye 20 containing two one way valves, inlet valve 22 to the device and exit valve 23 from the device. The valves are positioned to effect the proper movement of radioactive particles through provided conduits 30, 31. As shown in FIG. 1, when the patient inhales, the diaphragm 28 of the valve 23 opens and permits the radioactive particles to enter the mouthpiece and ultimately to deposit in the lungs. During inhalation, diaphragm 21 of the valve 22 remains closed due to the pressure differential across valve 22. At exhalation, the valve 23 closes and the valve 22 opens to permit the exhalant to pass the valve 22, travel through the conduit 30, and into an entrapping filter 40 (FIG. 4).

Figure 4:
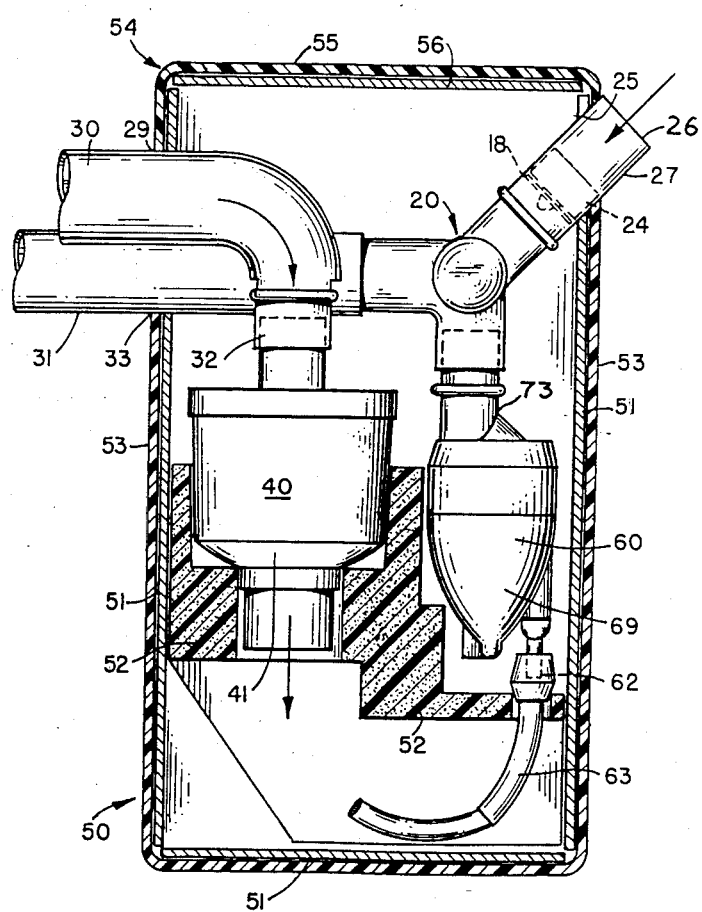
FIG. 4 is a fragmentary perspective diagramatic view of an apparatus which includes a portion of the apparatus of FIG. 1 illustrating the shielded container for the nebulizer and the entrapping filter.

FIG. 4 shows the operational technique as follows: The radiopharmaceutical liquid to be aerosolized is added to the system through the diaphragm 18 of valve 24 contained in wye leg 27. The wye leg 27 protrudes through shielded container 50 at portal 25, a downwardly extending slot being provided on the sidewall of the container 50 for this purpose. The entrance portal 26 to wye leg 27 is set at an angle to minimize direct radiation streaming from the solution of radioactive liquid contained in the baffled nebulizer 60 when the apparatus is in operation. The injected radioactive solution deposits in the baffled nebulizer 60 at approximate level 69. Oxygen from a tank (not shown) is directed into the system at approximately 10 liters per minute via a flexible tube 63 which is connected from the tank to the bottom of nebulizer 60 via tubular stem 62. The oxygen mixes with radioactive solution to form airborne particles. The airborne particles then pass through the conduit 31, through the valve 23, and into a patient's lungs. The exhaled air including aerosol passes through the valve 22 to the conduit 30, and into a filter 40 via tubular extension 32, and the aerosol becomes entrapped in the filter 40. The patient breathes the aerosolized radioactive particles until enough radiation from the patient's lungs is externally detected by sensing with radioactive detectors.

FIG. 2 illustrates the entry port 26 of radioactive solution that enters the baffled nebulizer 60. The radioactive solution to be aerosolized is carried to entry port 26 in a shielded syringe to minimize radiation exposures to the administering technician and patient (both not shown). The entry port 26, shown in FIG. 4 protrudes from side of the lead shielded container 50 (FIG. 4) at an approximate angle of forty-five degrees. The angulation of the entry port reduces the amount of radiation exposure to the administering technician due to streaming, once the radioactive solution has entered the nebulizer system. The solution enters the system through the diaphragm 18 of the valve 24. The needle of the syringe containing radioactive solution (not shown) pushes diaphragm 18 aside and while the orifice of the needle (not shown) protrudes past diaphragm 18, the radioactive solution is injected into the nebulizer system. The check valve 24 is approximately 22 millimeters in diameter. To ease patient's breathing, the valve 24 also acts as an inlet valve in that each time the patient inhales, he receives a portion of air from the atmosphere. In addition, the valve 24 acts as monitor to the patient's breathing function. The administering technician observes valve diaphragm 18 movement each time the patient inhales to insure patient is breathing normally.

FIG. 3 illustrates the nebulizer 60 fitted with an elongated conical baffle that permits proper sized radioactive particles to enter a patient's lungs. Oxygen enters the nebulizer 60 through the stem 62. The oxygen gas passes through a nozzle assembly 72 extending into the container 50. The nozzle assembly 72 includes gas nozzle 64 and coaxial solution nozzle 71 with approximately perpendicular positioned orifices. Extending above the nozzle assembly is an elongated conical settling baffle 65 formed of plastic and having a volume of approximately three cubic centimeters. The settling baffle 65 reduces hyperdeposition of large particles typically greater than two microns from entering the patient's lungs. The aerosolized radioactive particles enter the baffle area at the diffuser orifice of the gas nozzel 64 and through sedimentation, impaction, and turbulence within the baffle 65, particles greater than two microns settle to the interior bottom portion 68 of the nebulizer 60 and particles typically less than two microns enter conduit 73 (FIGS. 2,4) above the nebulizer 60 and are inhaled by the patient (not shown).

The top of the conical baffle 65 has a symmetrical opening 67 of approximately three millimeters in diameter that permits entry of conduit tubing 66 that carries radioactive solution from the nebulizer 60 reservoir to orifice 71. The radioactive solution exiting the orifice 71 mixes with incoming oxygen and is aerosolized through orifice-diffuser arrangement which includes a diffuser 74. The particles are properly sized while engaging in turbulent action within the baffle 65.

FIG. 4 illustrates the shielded container 50 which houses the entrapping filter 40, the baffled nebulizer 60 and a supporting insert 52. The container 50 has an approximate volume of three liters and consists of outer plastic laminate 53 and lead shielding 51 laminated together and comprising average thicknesses of two to four millimeters. The lead shielding is necessary to minimize radiation exposure to the administering technician and patient during the ventilation studies of the lung. Plastic or equivalent material insert 52 sets entrapping filter 40 in a fixed position using filter portion 41 as a seat. Baffled nebulizer 60 is seated in similar fashion using reservoir end portions defined by level 69 and the stem 62 thereof. Openings 29, 33 of approximately 25 millimeters in diameter are made through shielded container 50 to allow conduits 30, 31 and the oxygen tube 63 to exit the container. The additional opening 25 of approximately five millimeters is made through the container 50 exposing entry port or injection site of the radioactive solution. The angle of the opening 25 with respect to the horizontal is 90° and is made to minimize radiation streaming from shielded container 50. Cap 54 constructed or plastic laminate 55 and lead shielding 56 laminated together are of the previously described thickness of the plastic laminated 53 and the lead shielding 51. The cap 54 is removable to permit easy access and exit of the disposable device at commencement and termination of diagnostic procedures.

From the foregoing it will be seen that the pulmonary inhalation device of the present invention provides for a disposable device that generates properly sized radioactive particles having provisions for proper valving, proper shielding, and ease of operation. Further, the invention has been described with reference to particular embodiment, but it will be appreciated that variations within the spirit and scope of the invention will occur to those skilled in the art. For example, in FIG. 4, the oxygen tubing 63 could exit from another port in the container 50.

What is claimed is:

1. An aerosol inhalation device for supplying an aerosol mist to a subject, the device comprising first conduit means for providing an exclusive inhalation path and second conduit means for providing an exclusive exhalation path, mouthpiece means connected to the first and second conduit means, valve means for controlling inhalation solely via said first conduit means and exhalation solely via said second conduit means, respectively, a nebulizer coupled to said first conduit means, means in fluid communication with said nebulizer for allowing introduction of liquid into said nebulizer, means associated with said nebulizer for generating an aerosolized mist carrying airborne particles, means for introducing a mixture of air and the mist into said first conduit means, and entrapping filter means coupled to said second conduit means for removing the aerosol exhaled.

2. The aerosol inhalation device according to claim 1, wherein said means for allowing introduction of a liquid into said nebulizer comprises a one-way valve means in fluid communication with said nebulizer and with said first conduit means for permitting entry of atmospheric air into said nebulizer and into said first conduit means.

3. The aerosol inhalation device according to claim 2, wherein said one way valve means includes an observable movable member to permit observation of inhalation frequency of a subject.

4. The aerosol inhalation device according to claim 3, wherein said moveable member is a diaphragm of a one-way valve.

5. The aerosol inhalation device according to claim 4, wherein said means for allowing introduction of a liquid is a valve part allowing a needle to extend past said diaphragm of said one-way valve.

6. The aerosol inhalation device according to claim 1, including a settling baffle in said nebulizer to generate properly sized aerosol particles of less than substantially two microns.

7. The aerosol inhalation device according to claim 6, wherein said nebulizer includes a diffuser and gas orifice, said settling baffle being positioned above said diffuser and said gas orifice for permitting aerosol particles larger than substantially two microns to remain in said nebulizer.

8. An aerosol inhalation device for supplying an aerosol mist to a subject, the device comprising first conduit means for providing an exclusive inhalation path and second conduit means for providing an exclusive exhalation path, mouthpiece means connected to the first and second conduit means, valve means for controlling inhalation solely via said first conduit means and exhalation solely via said second conduit means, respectively, a nebulizer coupled to said first conduit means, means in fluid communication with said nebulizer for allowing introduction of liquid into said nebulizer, means associated with said nebulizer for generating an aerosolized mist carrying airborne particles, and means for introducing a mixture of air and the mist into said first conduit means.

9. The aerosol inhalation device according to claim 8, wherein said means for allowing introduction of a liquid into said nebulizer comprises a one-way valve means in fluid communication with said nebulizer and with said first conduit means for permitting entry of atmospheric air into said nebulizer and into said first conduit means.

10. The aerosol inhalation device according to claim 9, wherein said one way valve means includes an observable movable member to permit observation of inhalation frequency of a subject.

11. The aerosol inhalation device according to claim 10, wherein said moveable member is a diaphragm of a one-way valve.

12. The aerosol inhalation device according to claim 11, wherein said means for allowing introduction of a liquid is a valve part allowing a needle to extend past said diaphragm of said one-way valve.

13. The aerosol inhalation device according to claim 8, including a settling baffle in said nebulizer to generate properly sized aerosol particles of less than substantially two microns.

14. The aerosol inhalation device according to claim 13, wherein said nebulizer includes a diffuser and gas orifice, said settling baffle being positioned above said diffuser and said gas orifice for permitting aerosol particles larger than substantially two microns to remain in said nebulizer.

15. A disposable aerosol inhalation device which may be used in conjunction with a re-usable radiation shielding container for supplying an aerosol mist containing radioactive material to a subject, the disposable device comprising first and second conduit means, mouthpiece means connected to the first and second conduit means, valve means for controlling inhalation via said first conduit means to exclusion of said second conduit means and exhalation via said second conduit means to exclusion of said first conduit means, respectively, nebulizer coupled to said first conduit means for supplying an aerosol mist containing radioactive material thereto, means in fluid communication with said nebulizer for allowing introduction of liquid into said nebulizer, means associated with said nebulizer for generating an aerosolizer mist carrying airborne particles, means for introducing a mixture of air and the mist into said first conduit means, and entrapping filter means coupled to said second conduit means for removing the aerosol exhaled.

16. A disposable aerosol inhalation device which may be used in conjunction with a re-usable radiation shielding container for supplying an aerosol mist containing radioactive material to a subject, the disposable device comprising first and second conduit means, mouthpiece means connected to the first and second conduit means, valve means for controlling inhalation via said first conduit means to the exclusion of said second conduit means and exhalation via said second conduit means to exclusion of said second conduit means, respectively, a nebulized coupled to said first conduit means for supplying an aerosol mist containing radioactive material thereto, means in fluid communication with said nebulizer for allowing introduction of liquid containing radioactive material into said nebulizer, means associated with said nebulizer for generating an aersolized mist carrying airborne particles, and means for introducing a mixture of air and the mist into said first conduit means.

17. An aerosol inhalation device for supplying an aerosol mist to a subject, the device comprising first and second conduit means, mouthpiece means connected to the first and second conduit means, valve means for controlling inhalation via said first conduit means to exclusion of said second conduit means and exhalation via said second conduit means to exclusion of said first conduit means, respectively, a nebulizer coupled to said first conduit means for supplying an aerosol mist, means in fluid communication with said nebulizer for allowing introduction of liquid into said nebulizer, means associated with said nebulizer for generating an aerosolized mist, means for introducing a mixture of air and the mist into said first conduit means, and entrapping filter means coupled to said second conduit means for removing the aerosol exhaled.

18. An aerosol inhalation device for supplying an aerosol mist to a subject, the device comprising first and second conduit means, mouthpiece means connected to the first and second conduit means, valve means for controlling inhalation via said first conduit means to exclusion of said second conduit means and exhalation via said second conduit means to exclusion of said first conduit means, respectively, a nebulizer coupled to said first conduit means for supply an aerosol mist, means in fluid commmunication with said nebulizer for allowing introduction of liquid into said nebulizer, means associated with said nebulizer for generating an aerosolized mist, and means for introducing a mixture of air and the mist into said first conduit means.

* * * * *

REEXAMINATION CERTIFICATE (1708th)
United States Patent [19]
Bordoni et al.

[11] B1 4,598,704

[45] Certificate Issued May 26, 1992

[54] AEROSOL INHALATION DEVICE

[75] Inventors: Maurice E. Bordoni, Westtown; Ephraim Lieberman, Suffern, both of N.Y.

[73] Assignee: Cadema Medical Products, Inc., Middletown, N.Y.

Reexamination Request:
No. 90/002,136, Sep. 13, 1990

Reexamination Certificate for:
Patent No.: 4,598,704
Issued: Jul. 8, 1986
Appl. No.: 707,387
Filed: Mar. 1, 1985

Related U.S. Application Data

[60] Division of Ser. No. 642,718, Aug. 22, 1984, Pat. No. 4,510,929, which is a continuation of Ser. No. 360,370, Apr. 30, 1982, abandoned.

[51] Int. Cl.$^5$ .................. A61M 11/00; A61M 15/00; A61M 16/10; B05B 17/06
[52] U.S. Cl. .................. 128/200.14; 128/203.12; 128/203.25; 128/203.29; 128/200.18; 128/200.21
[58] Field of Search .............. 128/200.18, 200.14, 128/200.21, 203.12, 204.18, 203.25, 203.29

[56] References Cited

U.S. PATENT DOCUMENTS

| | | | |
|---|---|---|---|
| 1,263,079 | 4/1918 | Leon | 128/200.18 |
| 1,839,193 | 1/1932 | Blanchard | 128/200.18 |
| 2,605,764 | 8/1952 | Adams et al. | 128/200.18 |
| 3,172,406 | 3/1965 | Bird et al. | 128/200.18 |
| 3,353,536 | 11/1967 | Bird et al. | 128/200.18 |
| 3,584,621 | 6/1971 | Bird et al. | 128/200.18 |
| 3,664,337 | 5/1972 | Lindsey et al. | 128/200.18 |
| 3,724,454 | 4/1973 | Brown | 128/200.18 |
| 3,762,409 | 10/1973 | Lester | 128/200.14 |
| 3,771,721 | 11/1973 | Van Amerongen | 128/200.18 |
| 3,857,909 | 12/1974 | Huggins | 128/200.18 |
| 3,985,131 | 10/1976 | Buck et al. | 128/205.24 |
| 3,990,442 | 11/1976 | Patneau | 128/203.16 |
| 4,007,238 | 2/1977 | Glenn | 128/200.18 |
| 4,064,875 | 12/1977 | Cramer et al. | 128/205.12 |
| 4,106,503 | 8/1978 | Rosenthal et al. | 128/200.18 |
| 4,116,387 | 9/1978 | Kremer, Jr. et al. | 128/200.18 |
| 4,127,129 | 11/1978 | Cramer | 128/204.28 |
| 4,164,942 | 8/1979 | Beard et al. | 128/207.12 |
| 4,251,033 | 2/1981 | Rich et al. | 128/200.18 |
| 4,259,951 | 4/1981 | Chernack et al. | 128/205.24 |
| 4,333,450 | 6/1982 | Lester | 128/200.18 |
| 4,660,547 | 4/1987 | Kremer, Jr. | 128/200.18 |
| 4,803,977 | 2/1989 | Kremer, Jr. | 128/200.18 |

OTHER PUBLICATIONS

Hayes, et al., *Radiology*, "Improved Radioaerosol Administration System for Routine Inhalation Lung Imaging", Apr., 1979, pp. 256-258.

Wasnich, Richard D., *Journal of Nuclear Medicine*, "A High Frequency Ultrasound Nebulizer System for Radioaerosol Delivery", Aug. 1976, vol. 17, No. 8, pp. 737.

Taplin, G. V., et al., *Lung Perfusion-Inhalation Scintigraphy in Obstructive Airway Disease and Pulmonary Embolism*, Radiologic Clinics of North America, Dec. 1978; 16 (3): 491-513.

Taplin, G. V. et al., *Atlas for Lung Imaging Using Radioaerosols*, Dec. 1979; 2-E2.

Pircher, et al., *Journal of Nuclear Medicine*, "Aerosol Scans with Particles in the Submicronic Range", Aug. 1965, vol. 12, No. 6, pp. 385-386.

Mullins, et al., *Journal of Nuclear Medicine*, "Improved Technique for Aerosol Inhalation Scanning", Nov. 1972, vol. 12, No. 6, p. 872.

Swift, D. L., et al., *Size Distribution of DTPA Aerosols Produced in the Taplin-Elam Aerosol Inhalation Apparatus*, Feb. 1980: 1-12.

*Primary Examiner*—Edgar S. Burr

[57] ABSTRACT

A disposable aerosol inhalation device for use in producing properly sized radioactive tagged particles. A mouthpiece is attached to a wye connector containing a valving system for inhalation of the radioactive aerosol and exhalation to an entrapping filter. Conduits are respectively provided by flexible tubing to a nebulizer and to the filter. The optimum range of particle sizes is generated by producing an aerosol from the nebulizer having an internal baffle. For ease of handling and to minimize radiation exposures, an entry is provided to add radioactive solution directly into the baffled nebulizer. To further reduce radiation exposure, the baffled nebulizer and entrapping filter are housed in a leaded enclosure. A method, which may be carried out using the device and the leaded enclosure involves introducing radioactive solution into the nebulizer to generate an aerosolized mist containing radioactive tagged particles of less than substantially two microns.

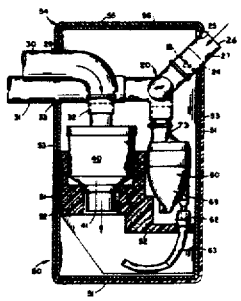

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 6–9, and 13–18 are cancelled.

Claims 3 and 10 are determined to be patentable as amended.

Claims 4, 5, 11, and 12, dependent on an amended claim, are determined to be patentable.

3. [The aerosol inhalation device according to claim 2] *An aerosol inhalation device for supplying an aerosol mist to a subject, the device comprising first conduit means for providing an exclusive inhalation path and second conduit means for providing an exclusive exhalation path, mouthpiece means connected to the first and second conduit means, valve means for controlling inhalation solely via said first conduit means and exhalation solely via said second conduit means, respectively, a nebulizer coupled to said first conduit means, means in fluid communication with said nebulizer for allowing introduction of liquid into said nebulizer, means associated with said nebulizer for generating an aerosolized mist carrying airborne particles, means for mixing ambient air with the mist, and for introducing said mixture into said first conduit means, and entrapping filter means coupled to said second conduit means for removing the aerosol exhaled, wherein said means for allowing introduction of a liquid into said nebulizer comprises a one-way valve means in fluid communication with said nebulizer and with said first conduit means for permitting entry of atmospheric air into said nebulizer and into said first conduit means, wherein said one way valve means includes an observable movable member to permit observation of inhalation frequency of a subject.*

10. [The aerosol inhalation device according to claim 9,] *An aerosol inhalation device for supplying an aerosol mist to a subject, the device comprising first conduit means for providing an exclusive exhalation path, mouthpiece means connected to the first and second conduit means, valve means for controlling inhalation solely via said first conduit means and exhalation solely via said second conduit means, respectively, a nebulizer coupled to said first conduit means, means in fluid communication with said nebulizer for allowing introduction of liquid into said nebulizer, means associated with said nebulizer for generating an aerosolized mist carrying airborne particles, and means for mixing ambient air with the mist, and for introducing said mixture into said first conduit means, wherein said means for allowing introduction of a liquid into said nebulizer comprises a one way valve means in fluid communication with said nebulizer and with said first conduit means for permitting entry of atmospheric air into said nebulizer and into said first conduit means, wherein said one way valve means includes an observable movable member to permit observation of inhalation frequency of a subject.*

* * * * *